(12) United States Patent
Matsumura

(10) Patent No.: US 6,702,441 B2
(45) Date of Patent: Mar. 9, 2004

(54) OPHTHALMIC MEASURING DEVICE

(75) Inventor: Isao Matsumura, Yokosuka (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/268,980

(22) Filed: Oct. 11, 2002

(65) Prior Publication Data

US 2003/0071987 A1 Apr. 17, 2003

(30) Foreign Application Priority Data

Oct. 17, 2001 (JP) ......................................... 2001-319564
Oct. 25, 2001 (JP) ......................................... 2001-327277

(51) Int. Cl.[7] .............................. A61B 3/14; A61B 3/10; G01B 9/00
(52) U.S. Cl. ........................ 351/214; 351/206; 356/124
(58) Field of Search ................................. 356/124–127; 351/205, 206, 214, 221

(56) References Cited

U.S. PATENT DOCUMENTS

| 4,572,627 | A | | 2/1986 | Madate et al. ............... 351/206 |
|---|---|---|---|---|
| 4,678,297 | A | | 7/1987 | Ishikawa et al. ............. 351/208 |
| 4,690,525 | A | | 9/1987 | Kobayashi et al. ........... 351/206 |
| 4,762,410 | A | | 8/1988 | Sekiguchi et al. ............ 351/206 |
| 4,867,554 | A | | 9/1989 | Matsumura ................... 351/205 |
| 4,917,458 | A | | 4/1990 | Matsumura ................... 354/212 |
| 4,999,009 | A | | 3/1991 | Matsumura ................... 351/212 |
| 5,018,851 | A | | 5/1991 | Matsumura ................... 351/214 |
| 5,886,768 | A | * | 3/1999 | Knopp et al. ................. 351/212 |
| 6,267,477 | B1 | * | 7/2001 | Karpol et al. ................ 351/221 |
| 6,520,640 | B1 | * | 2/2003 | Binnun .......................... 351/206 |
| 2001/0056277 | A1 | * | 12/2001 | Vinciguerra et al. ............ 606/5 |
| 2003/0038921 | A1 | * | 2/2003 | Neal et al. .................... 351/212 |

* cited by examiner

*Primary Examiner*—Michael P. Stafira
(74) *Attorney, Agent, or Firm*—Fitzpatrick, Cella, Harper & Scinto

(57) ABSTRACT

An ophthalmic measuring device for obtaining three-dimensional information of an eye to be examined without time lag by projecting pulsed light chirped in such a manner that color is continuously changed from the leading end through the tail end of a pulsed light with time on the eye to be examined, cutting out the pulsed light reflected from the eye to be examined at a predetermined timing by a shutter, and obtaining spectroscopic distribution characteristic of the cut-out image by a spectroscopic unit.

8 Claims, 10 Drawing Sheets

OPHTHALMIC MEASURING DEVICE

BACKGROUND OF THE INVENTION

1. Field of the Invention

The present invention relates to an ophthalmic measuring device using pulsed light chirped in such a manner that color is continuously changed from the leading end through the tail end of a pulsed light with time.

2. Description of the Related Art

In the ophthalmic measurement of the related art, a reference mark is projected on the eye to be examined, and then the distance or the shape of the eye to be examined is obtained from defocusing or position of the image of the reference mark reflected from the eye to be examined.

However, in the related art described above, a complicated mechanism using light scanning technology or the like is necessary to obtain three-dimensional information, and time lag due to scanning time is inevitable. In addition, there is a limit of measuring accuracy due to variations in intensity of reflected light from the eye to be examined or due to limits of accuracy of the reference mark.

SUMMARY OF THE INVENTION

It is an object of the present invention to provide an ophthalmic measuring device for obtaining three-dimensional information of the eye to be examined without time lag by the steps of projecting a pulsed light chirped in such a manner that color is continuously changed from the leading end through the tail end of the pulsed light with time on the eye to be examined, cutting out the pulsed light reflected from the eye to be examined by a shutter at a predetermined timing, and examining spectral distribution characteristics of the cut-out image by a spectroscope.

Further objects, features and advantages of the present invention will become apparent from the following description of the preferred embodiments (with reference to the attached drawings).

DESCRIPTION OF THE PREFERRED EMBODIMENTS

[First Embodiment]

Figure 1:
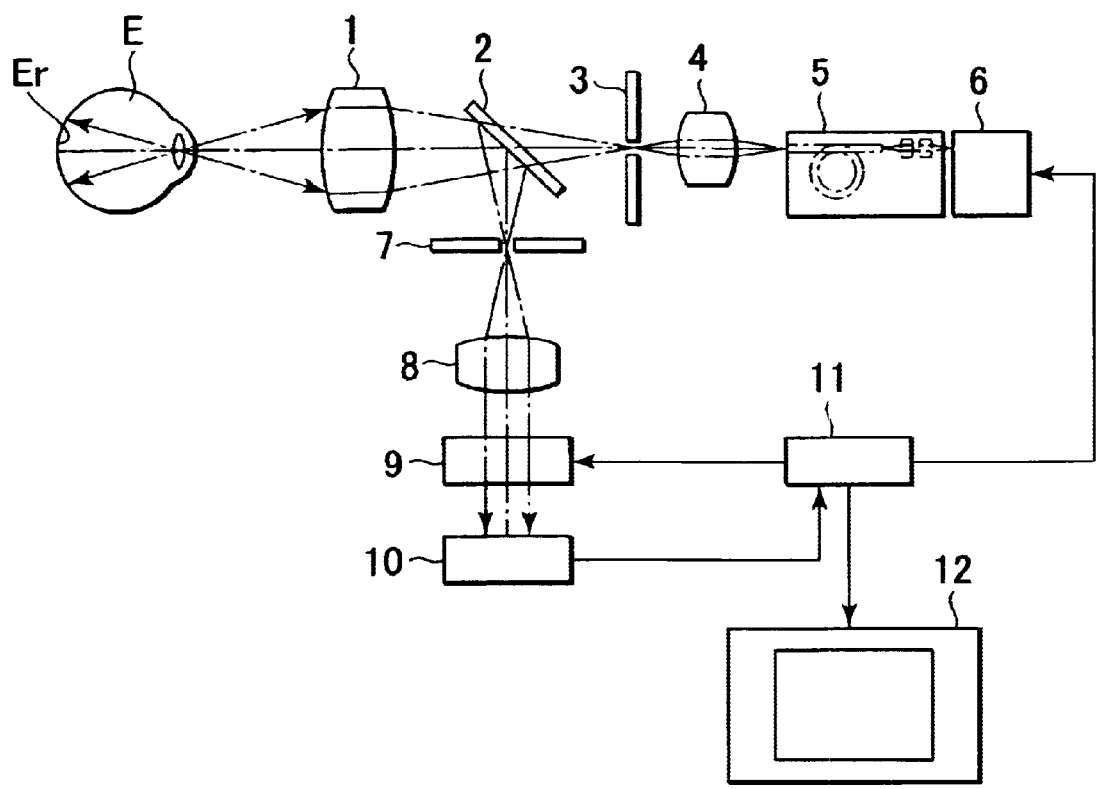
FIG. 1 is a block diagram of a ophthalmic measuring device according to a first embodiment.

Referring now to the drawings, embodiments of the invention will be described in detail.

FIG. 1 is a block diagram of a first embodiment. An objective lens 1, a beam splitter 2, an illuminating aperture diaphragm 3, a relay lens 4, a chirp light generating unit 5, and a mode locked ti-sapphire laser light source 6 for emitting ultra-short pulsed light are arranged in sequence forwardly of the eye to be examined E. A light receiving aperture diaphragm 7 disposed in conjugation with the illuminating aperture diaphragm 3, a projection lens 8, an ultra high-speed non-linear optical shutter 9 of carbon disulfide molecular liquid, and a two-dimensional color image pick-up unit 10 are arranged in sequence in the direction of reflection of the beam splitter 2. An output of a computing unit 11 for supplying timing signals for cutting out images at a certain timing is connected to the laser light source 6 and the ultra high-speed optical shutter 9.

The two-dimensional color image pick-up unit 10 is disposed at the position in conjugation with the eyeground Er of the eye to be examined E with respect to the objective lens 1, the beam splitter 2, the aperture diaphragm 7, the projection lens 8, and the ultra high-speed optical shutter 9.

The projection lens 8 is disposed in such a manner that the light receiving aperture diaphragm 7 coincides with the position of the front focus point for collecting light from the eyeground Er passed through the projection lens 8.

A pulsed light emitted from the laser light source 6 is guided while being blocked in the optical fiber having extremely thin core of high index of refraction in the chirp light generating unit 5 to generate non-linear optical effects and hence to cause frequency modulation of light pulses so that a pulsed light whereof the color varies regularly with time is generated. The pulsed light passed through the relay lens 4 and the illuminating aperture diaphragm 3, and then though the beam splitter is converged to the point near the iris of the eye to be examined E by the objective lens 1 and then is illuminated to the eyeground Er. The light reflected from the eyeground Er leaves the iris again and enters into the objective lens 1, and then is reflected from the beam splitter 2, passed through the light receiving aperture diaphragm 7, the projection lens 8, and the ultra high-speed optical shutter 9, and then projected on the two-dimensional color image pick-up unit 10. The pulsed light from the laser light source 6 is obtained at the timing sent from the computing unit 11, and the ultra high-speed optical shutter 9 is operated synchronously with the pulsed light. The computing unit 11 is connected to the image pick-up unit 10, and processes signals from the image pick-up unit to display three-dimensional information of the eye to be examined on the display unit 12.

Figure 2:
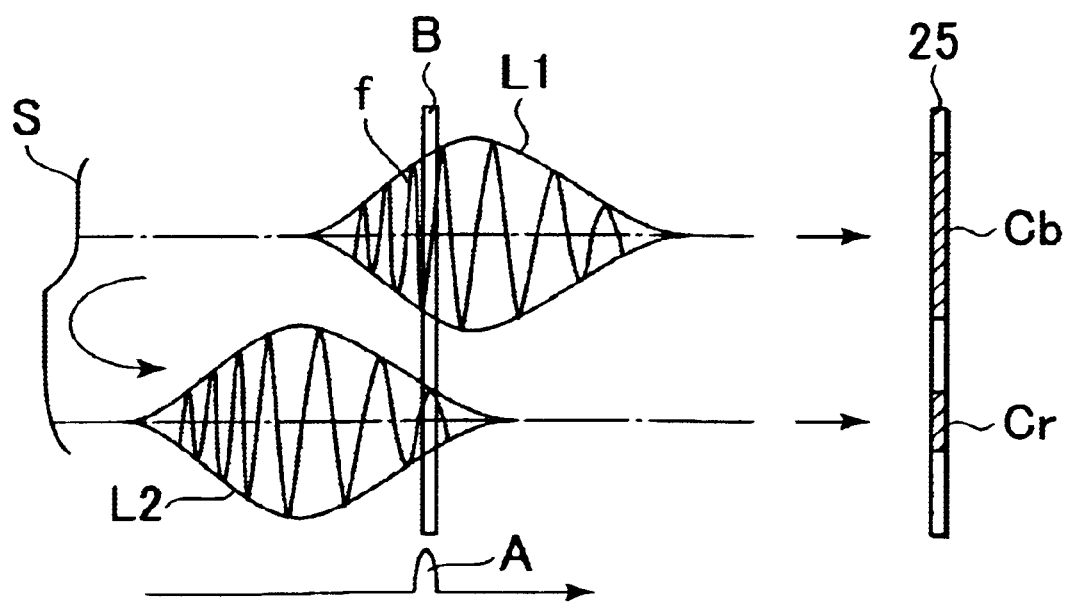
FIG. 2 is an explanatory drawing illustrating cutting-out of a color image from a reflected pulsed light.

FIG. 2 is an explanatory drawing illustrating cutting out of the color image obtained by the two-dimensional color image pick-up unit 10. The advanced position of a pulsed light reflected from the subject S differs depending on the height of the subject S. The pulsed light L1 reflected at the high position is ahead of the pulsed light L2 reflected at the lower position.

The chirp light has longer wavelength at the leading end than the tail end of the pulse. When focusing attention on the cut-off timing A on the cut-off timing axis, the pulsed light L1 reflected at the high position and the pulsed light L2 reflected at the low position have different frequencies f at the common cut-off position B, and in the cut-off two-dimensional image, the former generates a color image Cb closer to blue in comparison with the latter, while the latter generates a color image Cr closer to red in comparison with the former.

The color images Cb, Cr are to be displayed in contrast to the positional information of the subject S, and information of height or depth is only for the surface or a plane.

It is needless to say that the method of display is not limited to display in colors, but some other methods of display may also be employed. For example, it may be displayed by contours, numerous value, cross sections, or concentrations.

[Second Embodiment]

Figure 3:
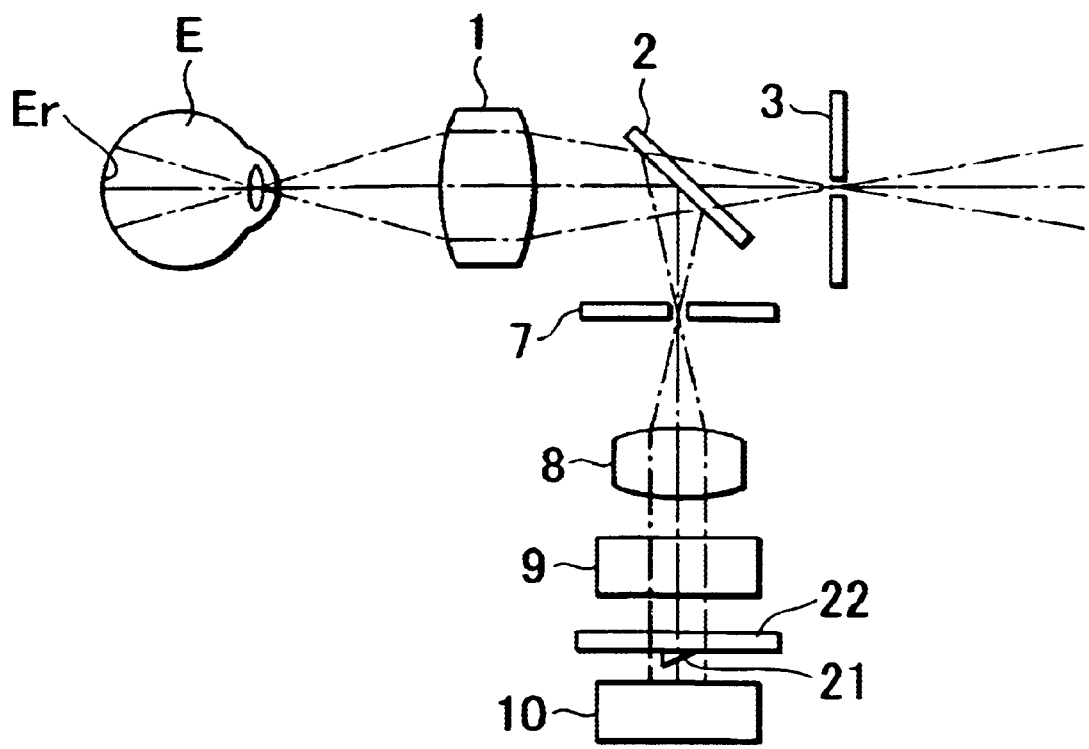
FIG. 3 is a block diagram of a ophthalmic measuring device according to a second embodiment.

FIG. 3 is a block diagram showing a multi-layer measuring system according to the second embodiment in which information of a plurality of items such as depth or distance are obtained. The same reference numerals as in FIG. 1 represent the same parts. A substrate 22 provided with a linear spectroscopic prism 21 is disposed between the ultra high-speed shutter 9 and the two-dimensional color image pick-up unit 10. The light source unit, that is, the ultra-short pulsed light generating portion is the same as the one in FIG. 1, and thus is omitted.

The pulsed light passed through the illuminating aperture diaphragm 3 passed through the beam splitter 2, and then converged at the point in the vicinity of the iris of the eye to be examined E by the objective lens 1, and then irradiated on the eyeground Er. The light reflected from the eyeground Er leaves the iris again and enters into the objective lens 1, and subsequently, is reflected from the beam splitter 2, then passes through the light receiving aperture diaphragm 7, the projection lens 8, the ultra high-speed optical shutter 9, and the linear spectroscopic prism 21 on the substrate 22 and then projected on the two-dimensional color image pick-up unit 10.

In FIG. 2, when the pulsed light L1 reflected at the high position and the pulsed light L2 reflected at the low position are on the same advancement axis, that is, in the case of multi-layer measurement, the pulsed light L1 reflected at the high position and the pulsed light L2 reflected at the low position are aligned. Therefore, though one is at the position ahead of the other, they cannot be separated by the two-dimensional color image pick-up unit 10 in this case.

Figure 4:
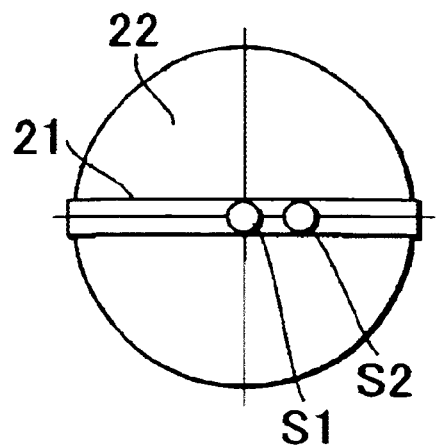
FIG. 4 is a front view of a linear spectroscopic prism.
Figure 5:
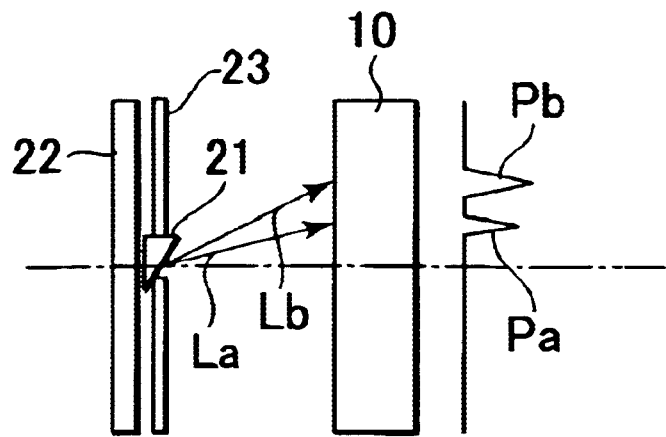
FIG. 5 is a drawing showing a principle of two-layer measurement using the linear spectroscopic prism.

FIG. 4 is a front view of the linear spectroscopic prism 21, and FIG. 5 is an explanatory drawing of a two-layer measurement. The portion other than the spectroscopic prism 21 on the front surface of the substrate 22 is covered by a douser 23. For example, when the subject S is double-layer structure, the light from the eyeground Er is separated toward two directions that are appropriate to an apex angle of the spectroscopic prism 21 such as a red beam La and a blue beam Lb by the spectroscopic prism 21, and then recognized as a red image signal Pa, and a blue image signal Pb in the two-dimensional color image pick-up unit 12. The amount of separation will be the extent corresponding to the position thereof in the second coordinate S2 as well.

Information of the depth or the height on the line corresponding to the length of the linear spectroscopic prism 21 may be obtained by covering the portion other than the spectroscopic prism 21 by the douser 23 in this state as shown in FIG. 5.

Figure 6:
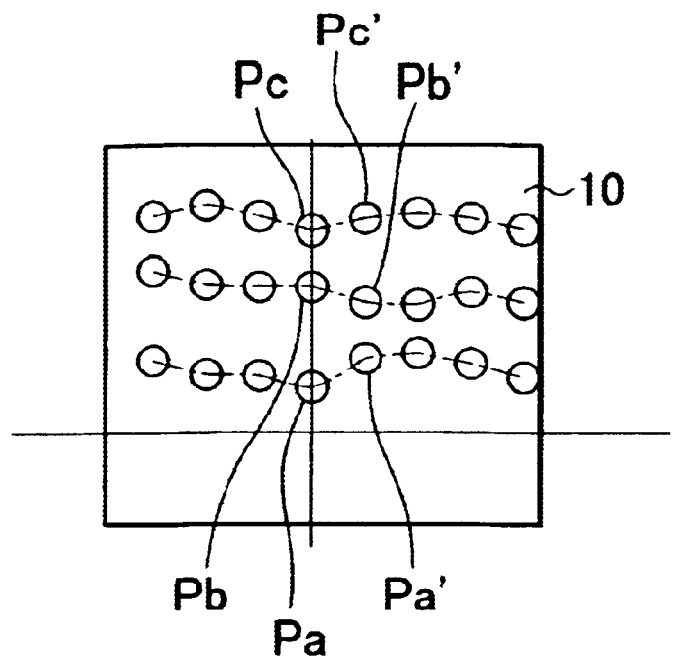
FIG. 6 is an explanatory drawing illustrating each layer on the two-dimensional color image pick-up unit in the case in which the object to be examined S has three-layer structure.

The case in which the subject S has a two-layer structure is described in this embodiment, when the number of layer is more than two, the number of color separations corresponds to the number of layers. FIG. 6 shows each layer on the two-dimensional color image pick-up unit 10 in the case where the subject S has a three-layer structure. The three-layer structure on the meridians of eye can be numerically obtained by obtaining the positions of the tree-layers Pa, Pb, Pc in the first coordinate, the positions of the three-layers Pa', Pb', Pc' in the second coordinate, and the positions of the three-layers from the third coordinate on. The number of layers is not limited thereto, but analysis of the multi-layer structure is possible.

Figure 7:
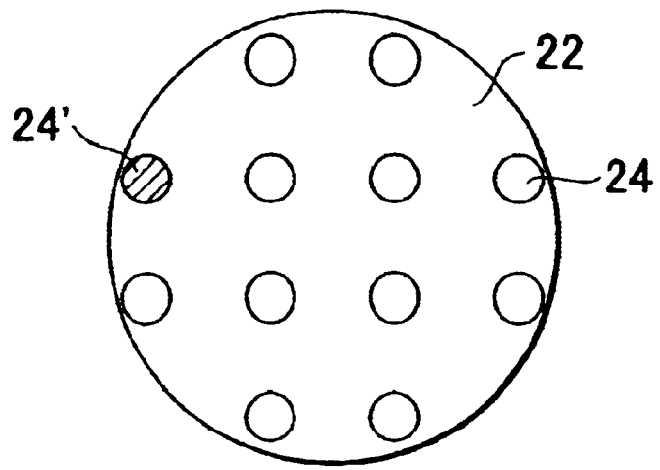
FIG. 7 is a front view of a number of prism blocs arranged on a substrate.
Figure 8:
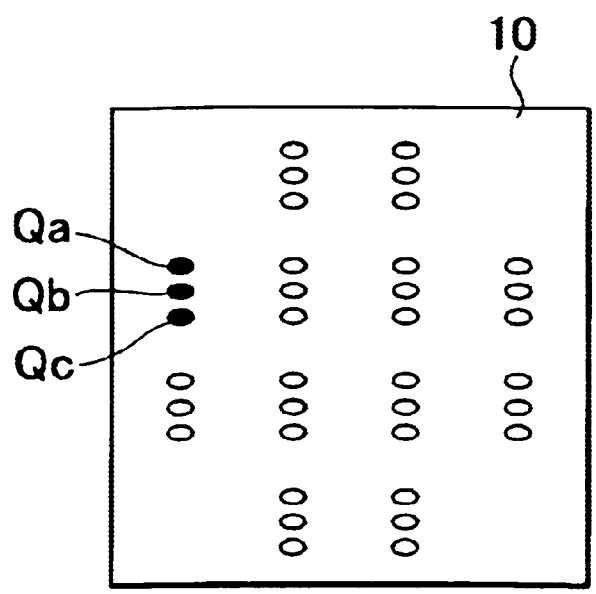
FIG. 8 is an explanatory drawing illustrating the positions of coordinates on the two-dimensional color image pick-up unit.

FIG. 7 shows a state in which a number of prism blocks 24 are regularly arranged on the substrate 22 instead of a linear spectroscopic prism 21. In this case, separation by the number of the layers may be performed by the prism block 24 at this position. For example, the three-layer separated image generated by the prism block 24' is represented as the coordinate Qa, Qb, Qc on the two-dimensional color image pick-up unit 10 shown in FIG. 8, and the same results may be obtained from other prism blocks 24 arranged regularly.

The same effect is expected by using a Fresnel prism instead of arranging the prism blocks 24, and shielding the position other than the coordinate to be measured by the douser 22.

[Third Embodiment]

Figure 9:
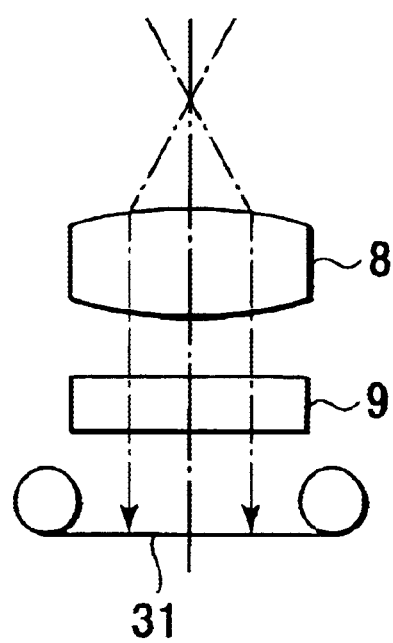
FIG. 9 is a block diagram of a ophthalmic measuring device according to a third embodiment.

FIG. 9 shows a third embodiment in which a color film 31 is disposed instead of the two-dimensional color image pick-up unit 10, and the color image is picked up by the color film 31. Further detailed positional coordinate and the map of the distance or the depth of the image recorded on the color film 31 may be created by analyzing the color of the image by a spectroscope.

Figure 10:
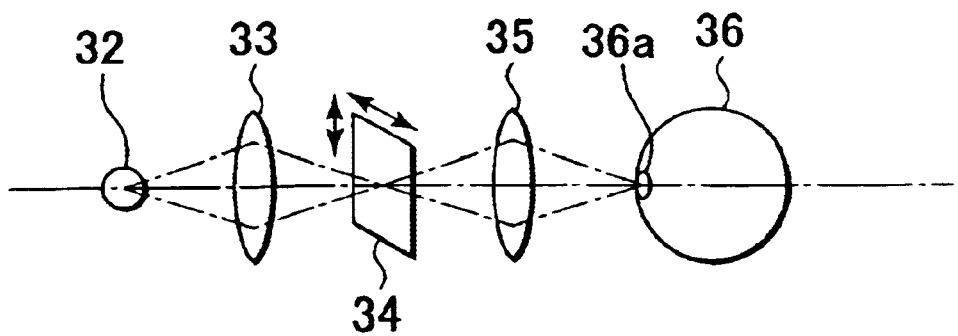
FIG. 10 is an explanatory drawing of a color film analysis unit.

FIG. 10 is a block diagram of the analyzing apparatus for images on the color film. A condenser lens 33, a color film 34, an imaging lens 35, and a spectroscope 36 are arranged forwardly of the while color light source 32.

The light from a white light source 32 is converted on the color film 34 via the condenser lens 33, and illuminated and spotlighted. The light passed through the color film 34 enters into the spectroscope 36 via a light-beam pick-up window 36a and then split up.

Spectroscopic information by each coordinate may be obtained from the whole color film 34 by performing flat bed scanning on the plane of the color film 34. This spectroscopic information allows obtaining of the layer structure on the plane or the solid structure with respect to the color information and the layer structure of the subject S.

Figure 11:
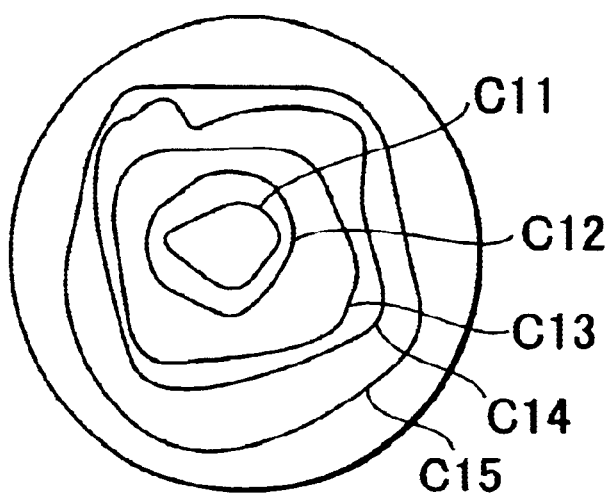
FIG. 11 is an explanatory drawing illustrating distribution of color images as mapped out in contours.
Figure 12:
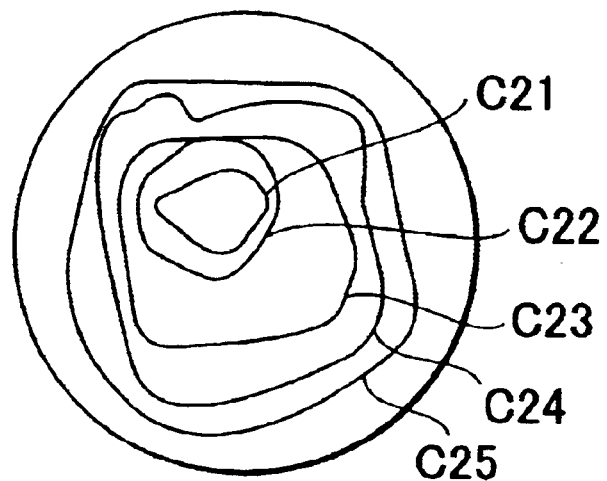
FIG. 12 is an explanatory drawing illustrating distribution of color images as mapped out in contours.
Figure 13:
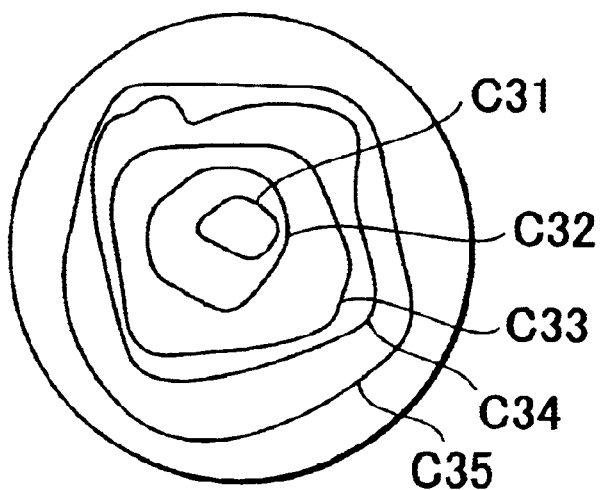
FIG. 13 is an explanatory drawing illustrating distribution of color images as mapped out in contours.

FIG. 11, FIG. 12, and FIG. 13 respectively represent color image distributions on the color film 34 as mapped out in contours by each of three layers. They are represented by, depending on the height of the plane of reflection, a first contour C11, a second contour C12, a third contour C13, a fourth contour C14, and a fifth contour C15 on the first layer, a first contour C21, a second contour C22, a third contour C23, a fourth contour C24, and a fifth contour C25 on the second layer, and a first contour C31, a second contour C32, a third contour C33, a fourth contour C34, and a fifth contour C35 on the third layer.

Figure 14:
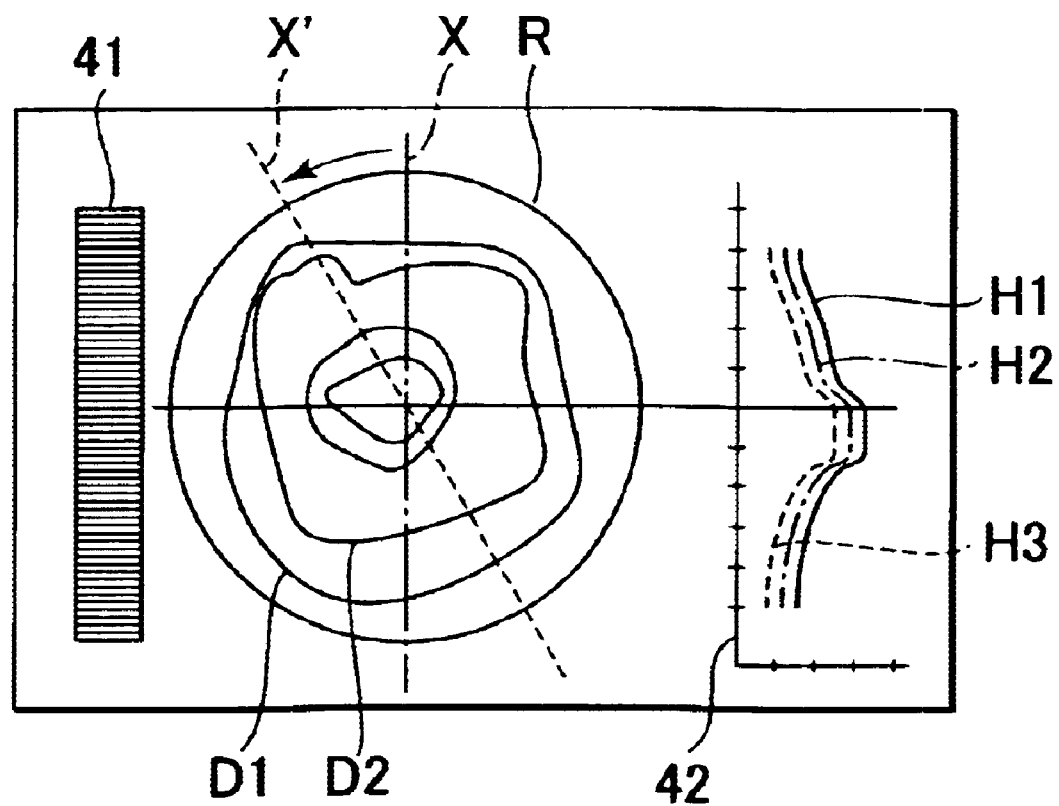
FIG. 14 is an explanatory drawing illustrating distribution of color images of a color film as mapped out in contours.

FIG. 14 represent color image distributions on the color film 34 as mapped out in contours by each of three layers. A plurality of color distributions D1, D2 are displayed in the imaging region R as a first layer. Such color distributions D are converted into height information, and the detailed relation between the color and the height is displayed on a color scale 41.

The height information may be displayed as values in various cross sections. For example, the height of the cross section X is displayed by a scale 42 and a linear elevation H1.

Given that it is three-layer display for example, the color distribution may be displayed by each layer by switching operation. In the cross section X, it may be displayed as, for example, a linear elevation H2 or a linear elevation H3 after being combined with the linear elevation H1. The cross section may be selected freely in rotation. When the second cross section X' is selected, a linear elevation corresponding thereto is displayed. It is also possible to display the image of the eyeground, which is the object to be measured, with the contour display of the color image distribution overlapped thereon.

[Fourth Embodiment]

Figure 15:
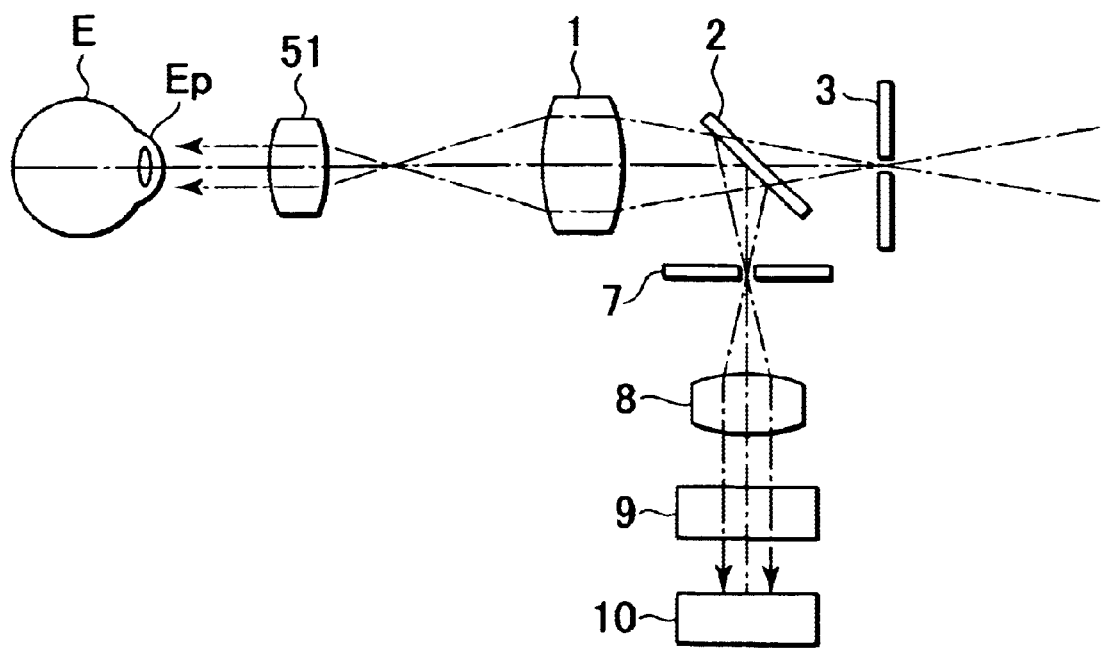
FIG. 15 is a block diagram of a fourth embodiment.

FIG. 15 shows a fourth embodiment using an afocal light receiving system, which is capable of measuring the anterior ocular segment. The same reference numerals as those in FIG. 1 represent the same parts in the optical system. An adapter lens 51 is disposed between the objective lens 1 and the eye to be examined E. The anterior ocular segment Ep of the eye to be examined is to be disposed at the position in conjugation with the two-dimensional color image pick-up unit 10 with respect to the adapter lens 51, the objective lens 1, the beam splitter 2, the light receiving aperture diaphragm 7, the projection lens 8, and the ultra high-speed non-linear optical shutter 9.

The light from the illuminating aperture diaphragm 3 is, after passing through the beam splitter 2, converged once by the objective lens 1, and then converted into a parallel light by the adapter lens 51 disposed so that the converging portion coincides with the rear focal point. Subsequently, it proceeds toward the eye to be examined E, and is reflected from the anterior ocular segment Ep.

The light reflected from the anterior ocular segment Ep passes again through the adapter lens 51, enters into the objective lens 1, reflects from the beam splitter 2, passes through the light receiving aperture diaphragm 7, the projection lens 8, and the ultra high-speed non-linear optical shutter 9, and is projected on the two-dimensional color image pick-up unit 10. By cutting out this reflected light at a certain timing by the computing unit 11, the two-dimensional color image having color distribution corresponding to the configuration of the anterior ocular segment Ep may be obtained.

Handling and display of the image may be performed in accordance with the description in conjunction with FIG. 3 through FIG. 14.

As is described thus far, according to the invention, necessity of mechanical mechanisms such as a light scanning mechanism may be eliminated, and time lag hardly occurs. In addition, the invention enables provision of three-dimensional information of the eyeground, which is improved in terms of accuracy.

While the present invention has been described with reference to what are presently considered to be the preferred embodiments, it is to be understood that the invention is not limited to the disclosed embodiments. On the contrary, the invention is intended to cover various modifications and equivalent arrangements included within the spirit and scope of the appended claims. The scope of the following claims is to be accorded the broadest interpretation so as to encompass all such modifications and equivalent structures and functions.

What is claimed is:

1. An ophthalmic measuring device for obtaining three-dimensional information of an eye to be examined, comprising:

a light projecting optical system including an unit for projecting a series of pulsed light whereof color changes continuously from the leading end to the tail end toward the eye to be examined;

a light receiving optical system for receiving said pulsed light reflected from a predetermined portion of the eye to be examined;

a shutter unit disposed in said light receiving optical system for cutting out said pulsed light reflected from the eye to be examined at a predetermined timing;

a color image pick-up unit disposed at the position substantially in conjugation with said predetermined portion of the eye to be examined with respect to said light receiving optical system for receiving said pulsed light cut-out by said shutter unit; and a computing unit for computing three-dimensional information of the eye to be examined from an image picked up by said color image pick-up unit and displaying on a display unit.

2. An ophthalmic measuring device according to claim 1, wherein said three-dimensional information is represented by color information or contours.

3. An ophthalmic measuring device according to claim 1, wherein said light projecting optical system includes an objective lens, and a first aperture diaphragm disposed substantially in conjugation with an anterior ocular segment of the eye to be examined with respect to said objective lens; and said light receiving optical system includes a second aperture diaphragm disposed substantially in conjugation with said anterior ocular segment of the eye to be examined with respect to said objective lens, and a projection lens disposed in such a manner that said second aperture diaphragm coincides with the position the front focal point.

4. An ophthalmic measuring device according to claim 1, further comprising:

a spectroscopic unit;

wherein three-dimensional information in multi-layer structure may be obtained by splitting a series of pulsed light reflected from said eye to be examined toward the light receiving optical system.

5. An ophthalmic measuring device according to claim 1, wherein said light projecting unit is a femtosecond laser light source.

6. An ophthalmic measuring device according to claim 1, wherein a detachable objective auxiliary lens is disposed between said objective lens and the eye to be examined.

7. An ophthalmic measuring device according to claim 1, wherein the predetermined position of the eye to be examined is the eyeground or the anterior ocular segment.

8. An ophthalmic measuring device for obtaining three-dimensional information of an eye to be examined, comprising:

a light projecting optical system including an unit for projecting a series of pulsed light whereof color changes continuously from the leading end to the tail end toward the eye to be examined;

a light receiving optical system for receiving said pulsed light reflected from a predetermined portion of the eye to be examined;

a shutter unit disposed in said light receiving optical system for cutting out said pulsed light reflected from the eye to be examined at a predetermined timing; and a color film disposed at the position substantially in conjugation with said predetermined portion of the eye to be examined with respect to said light receiving optical system for receiving said pulsed light cut out by said shutter unit and recording the same, wherein three-dimensional information of the eye to be examined may be obtained by analyzing said recorded color film image.

* * * * *

UNITED STATES PATENT AND TRADEMARK OFFICE
CERTIFICATE OF CORRECTION

PATENT NO. : 6,702,441 B2
DATED : March 9, 2004
INVENTOR(S) : Isao Matsumura

Page 1 of 1

It is certified that error appears in the above-identified patent and that said Letters Patent is hereby corrected as shown below:

Column 4,
Line 2, "layer" should read -- layers --.
Line 8, "tree-layers" should read -- three-layers --.
Line 38, "while" should read -- white --.
Line 61, "represent" should read -- represents --.

Column 5,
Line 5, "it is" should read -- it is a --.

Column 6,
Lines 1 and 57, "an" should read -- a --.
Line 16, "cut-out" should read -- cut out --.
Line 36, "position" should read -- position of --.
Line 40, "unit;" should read -- unit, --.
Line 41, "in" should read -- in a --.

Signed and Sealed this

Twenty-eighth Day of December, 2004

JON W. DUDAS
*Director of the United States Patent and Trademark Office*